United States Patent [19]

Zarchy et al.

[11] Patent Number: 5,245,102

[45] Date of Patent: * Sep. 14, 1993

[54] ISOMERIZATION WITH DISTILLATION AND PSA RECYCLE STREAMS

[75] Inventors: Andrew S. Zarchy, Amawalk, N.Y.; Martin F. Symoniak, Greensboro, N.C.

[73] Assignee: UOP, Des Plaines, Ill.

[*] Notice: The portion of the term of this patent subsequent to Sep. 8, 2009 has been disclaimed.

[21] Appl. No.: 929,237

[22] Filed: Aug. 14, 1992

Related U.S. Application Data

[63] Continuation of Ser. No. 619,556, Jan. 29, 1990, Pat. No. 5,146,037.

[51] Int. Cl.$^5$ .............................................. C07L 5/13
[52] U.S. Cl. .................................. 585/738; 585/734; 585/748; 585/751
[58] Field of Search ................. 585/734, 738, 748, 751

[56] References Cited

U.S. PATENT DOCUMENTS

| | | | |
|---|---|---|---|
| 2,966,528 | 12/1960 | Haensel | 260/666 |
| 3,175,444 | 3/1965 | Spinney | 83/251 |
| 3,755,144 | 8/1973 | Asselin | 208/95 |
| 4,709,116 | 11/1987 | Zarchy et al. | 585/738 |
| 4,709,117 | 11/1987 | Gray, Jr. | 585/738 |
| 4,717,784 | 1/1988 | Stem et al. | 585/738 |
| 4,804,802 | 2/1989 | Evans et al. | 585/734 |

OTHER PUBLICATIONS

The Handbook of Petroleum Refining Processes, edited by Robert A. Meyers, published by McGraw Hill Book Company (1986), pp. 5-49 through 5-51.

Primary Examiner—Anthony McFarlane
Assistant Examiner—Nhat D. Phan
Attorney, Agent, or Firm—Thomas K. McBride; John G. Tolomei

[57] ABSTRACT

An isomerization zone process is disclosed that combines a deisohexanizer with a PSA separation section to provide a product stream comprising methylbutane and dimethylbutane. The process combines a methylpentane and normal hexane recycle stream, a normal pentane recycle stream and a fresh feedstream to provide a combined feedstream that is charged to an isomerization zone. The effluent from the isomerization zone is stabilized and passed to a deisohexanizer. A sidecut stream carries the methylpentane and normal hexane recycle stream from the deisohexanizer. Hydrocarbons having a higher boiling point than the sidecut stream are withdrawn as a bottoms stream from the deisohexanizer. An overhead carries normal pentane, methylbutane and dimethylbutanes to the PSA separation section. An extract stream is recovered as the normal pentane recycle stream. The raffinate from the PSA provides a high octane isomerate stream comprising mainly methylpentane and dimethylbutanes.

10 Claims, 4 Drawing Sheets

ISOMERIZATION WITH DISTILLATION AND PSA RECYCLE STREAMS

CROSS-REFERENCE TO RELATED APPLICATIONS

This application is a continuation in part of U.S. Ser. No. 619,556, filed Nov. 29, 1990, now U.S. Pat. No. 5,146,037.

BACKGROUND OF THE INVENTION

This invention relates generally to the isomerization of hydrocarbons. This invention relates more specifically to the isomerization of light paraffins using a solid catalyst, and the separation of more highly branched paraffins from less highly branched paraffins by adsorptive separation.

DESCRIPTION OF THE PRIOR ART

High octane gasoline is required for modern gasoline engines. Formerly it was common to accomplish octane number improvement by the use of various lead-containing additives. As lead was phased out of gasoline for environmental reasons, octane ratings were maintained with other aromatic and low vapor pressure hydrocarbons. Environmental damage caused by the vaporization of low vapor pressure hydrocarbons and the health hazards of benzene in motor fuel will lead to further restrictions on octane blending components. Therefore, it has become increasingly necessary to rearrange the structure of the $C_5$ and $C_6$ hydrocarbons used in gasoline blending in order to obtain high octane levels. Catalytic isomerization is a widely used process for this upgrading.

The traditional gasoline blending pool normally includes $C_4$ and heavier hydrocarbons having boiling points of less than 205° C. (395° F.) at atmospheric pressure. This range of hydrocarbon includes $C_4$–$C_6$ paraffins and especially the $C_5$ and $C_6$ normal paraffins which have relatively low octane numbers. The $C_4$–$C_6$ hydrocarbons have the greatest susceptibility to octane improvement by lead addition and were formerly upgraded in this manner. With eventual phase out of lead additives octane improvement was obtained by using isomerization to rearrange the structure of the paraffinic hydrocarbons into branched-chain paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branched-chain isoparaffins. Although the $C_6$ and heavier hydrocarbons can be upgraded into aromatics through hydrocyclization, the conversion of $C_6$'s to aromatics creates higher density species and increases gas yields with both effects leading to a reduction in liquid volume yields. Moreover, the health concerns related to benzene are likely to generate overall restrictions on benzene and possibly aromatics as well, which some view as precursors for benzene tail pipe emissions. Therefore, it is preferred to charge the $C_6$ paraffins to an isomerization unit to obtain $C_6$ isoparaffin hydrocarbons. Consequently, octane upgrading commonly uses isomerization to convert $C_6$ and lighter boiling hydrocarbons.

The effluent from an isomerization reaction zone will contain a mixture of more highly branched and less highly branched paraffins. In order to further increase the octane of the products from the isomerization zone, normal paraffins, and sometimes less highly branched isoparaffins, are typically recycled to the isomerization zone along with the feedstream in order to increase the ratio of less highly branched paraffins to more highly branched paraffins entering the isomerization zone. A variety of methods are known to treat the effluent from the isomerization zone for the recovery of normal paraffins and monomethyl-branched isoparaffins for recycling for recycling these less highly branched paraffins to the isomerization zone.

Relatively higher octane isomers are commonly separated from lower octane normal paraffins and monomethyl-branched paraffins by using a distillation zone, adsorptive separation or some combination thereof. General arrangements for the separation and recycling of $C_5$ and $C_6$ hydrocarbons in isomerization units are shown and described at pages 5–49 through 5–51 of *The Handbook of Petroleum Refining Processes*, edited by Robert A. Meyers, published by McGraw Hill Book Company (1986). Distillation is a primary method of recovering the normal paraffins from the higher octane isomers. However, it is difficult to obtain a high octane product with distillative separation due to the boiling points of the various $C_5$ and $C_6$ hydrocarbons. With distillation the high octane dimethylbutanes and isopentanes cannot be economically recovered without also recovering relatively low octane normal pentane. Until recently the adsorptive separation processes were mainly used to separate normal paraffins from isoparaffins. Therefore, all isoparaffins were collected in a common extract stream that includes dimethylbutane and isopentanes as well as lower octane monomethylhexanes.

U.S. Pat. No. 2,966,528, issued to Haensel, discloses a process for the isomerization of $C_6$ hydrocarbons and the adsorptive separation of normal hydrocarbons from branched-chain hydrocarbons. The process adsorbs normal hydrocarbons from the effluent of the isomerization zone and recovers the unadsorbed hydrocarbons as product, desorbs straight-chain hydrocarbons using a normal paraffin desorbent, and returns the desorbent and adsorbed straight-chain hydrocarbons to the isomerization zone.

Many methods of separating normal paraffins from isoparaffins use adsorptive separation under liquid phase conditions. In such methods, the isomerization effluent contacts a solid adsorbent having a selectivity for normal paraffins to effect the selective adsorption of normal paraffins and allow recovery of the isoparaffins as a high octane product. Contacting the normal paraffin containing adsorbent with the desorbent material in a desorption step removes normal paraffins from the adsorbent for recycle to the isomerization zone. Both the isoparaffin and normal paraffin containing streams undergo a separation for the recovery of desorbent before the isoparaffins are recovered as a product and the normal paraffins recycled to the isomerization zone. Liquid phase adsorption has been carried out in conventional swing bed systems as shown in U.S. Pat. No. 2,966,528. The use of simulated moving bed systems for the selective adsorption of normal paraffins is also known and disclosed by U.S. Pat. No. 3,755,144. Simulated moving bed systems have the advantage of increasing recovery and purity of the adsorbed and nonadsorbed components in the isomerization zone effluent for a given unit of adsorbent material.

Adsorption processes using vapor phase adsorption for the separation of normal and branched paraffins are also well known. Examples of such processes are described in U.S. Pat. No. 3,175,444, issued to Kiyonaga, U.S. Pat. No. 4,709,116, issued to Zarchy et. al., and U.S. Pat. No. 4,709,117, issued to Gray. These references teach the use of multiple adsorbent vessels and the steps of adsorbing and desorbing the normal paraffins from an isomerization zone effluent. In addition, one or more steps of blowdown or void space purging are also taught to increase the recovery of product hydrocarbons.

Recent efforts in adsorptive separation teach adsorbents and flow schemes for also separating monomethyl paraffins from dimethyl-branched paraffins. U.S. Pat. No. 4,717,784 and 4,804,802 disclose processes for the isomerization of a hydrocarbon feed and the use of multiple adsorptive separations to generate normal paraffin and monomethyl-branched paraffin recycle streams. In such systems the effluent from the isomerization zone enters a molecular sieve separation zone that contains a 5A-type sieve and a ferrierite-type sieve that adsorb normal paraffins and monomethyl-branched paraffins, respectively. U.S. Pat. No. 4,804,802 discloses steam or hydrogen as the desorbent for desorbing the normal paraffins and monomethyl-branched paraffins from the adsorption section and teaches that steam or hydrogen may be recycled with the normal paraffins or monomethyl-branched paraffins to the isomerization zone.

Another method of recovering the high octane isomers from lower octane isomers and normal paraffins uses adsorptive separation followed by distillation. U.S. Pat. No. 3,755,144 shows a process for the isomerization of a pentane/hexane feed and the separation of normal paraffins from the isomerization zone effluent. The isomerization zone effluent is separated by a molecular sieve separation zone that includes facilities for the recovery of desorbent from the normal paraffin containing stream that is recycled to the isomerization zone. An extract stream that contains isoparaffins is sent to a deisohexanizer column that separates isopentane and dimethylbutane as a product stream and provides a recycle stream of isohexane that is returned to the isomerization zone.

It is an object of this invention to recycle low octane normal paraffins and monomethyl-branched paraffins to an isomerization zone in a more efficient manner.

It is a further object of this invention to increase the octane number of a product stream that can be obtained from a combination of an isomerization process, a distillation zone and an adsorptive separation zone for the production of high octane gasoline blending components.

It is a yet further object of this invention to improve processes for the recovery of low octane isomers from a $C_5$ and $C_6$ isomerization process.

SUMMARY OF THE INVENTION

Applicants have discovered that the octane numbers of $C_5$ and $C_6$ hydrocarbons can be significantly improved in a simple manner with an isomerization process that uses a specific separation arrangement for the recovery of methylpentane and dimethylbutanes and the recycle of lower octane methylpentanes, normal hexane and normal pentane. This process is the first to disclose an isomerization arrangement where the effluent from the isomerization zone passes first to a deisohexanizer zone and an adsorptive separation zone that operates to provide a low purity normal pentane recycle stream from the overhead of the deisohexanizer zone. In this manner, the deisohexanizer zone provides a recycle stream that contains methylpentanes, normal hexane and higher boiling hydrocarbons while the adsorptive separation section provides the low purity normal pentane stream which is combined with the recycle stream and a fresh feed to form a combined feed that enters the isomerization zone. A product stream comprising methylbutane and dimethylbutanes are recovered as the raffinate or non-adsorbed components from the adsorptive separation zone. The deisohexanizer zone also provides a bottoms stream containing cyclohexane and higher boiling hydrocarbons that are recovered for further processing.

Accordingly in one embodiment, this invention is a process for the isomerization of a feedstream that comprises $C_5$ and $C_6$ hydrocarbons. The process charges a first recycle stream, a second recycle stream and at least a portion of the $C_5$ and $C_6$ hydrocarbons contained in the feedstream into an isomerization zone and into contact with an isomerization catalyst at isomerization conditions effective to increase the branching of the hydrocarbons charged thereto and to produce an isomerization zone effluent stream that comprises normal pentane, normal hexane, methylbutane, dimethylbutane and methylpentane. At least a portion of the effluent from the isomerization zone flows to a deisohexanizer zone where it is distilled at conditions effective to produce an overhead stream comprising methylbutane, normal pentane and dimethylbutane; a bottoms stream having a boiling point at least greater than normal hexane and a sidecut stream comprising normal hexane and methylpentane. The overhead from the deisohexanizer column passes to a selective adsorption zone where it is contacted with an adsorbent and separated into an extract stream comprising normal hydrocarbons and a product stream comprising branched hydrocarbons. At least a portion of the extract stream and of the sidecut stream are then returned to the isomerization step as the first and second recycle streams.

In a further embodiment, this invention is a process for the isomerization of a feedstream that comprises $C_5$–$C_6$ hydrocarbons. The process includes the steps of combining at least a portion of a feedstream comprising $C_5$ and $C_6$ hydrocarbons, a first recycle stream and a second recycle stream to form a combined feedstream. The combined feedstream is charged to an isomerization zone and contacted with an isomerization catalyst at isomerization conditions effective to increase the branching of the combined feedstream hydrocarbons and to produce an isomerization effluent stream that comprises normal pentane, normal hexane, methylbutane, dimethylbutane and monomethylpentane. At least a portion of the isomerization zone effluent is passed to an inlet located at an intermediate point in a deisohexanizer column operated at conditions effective to distill this stream and to produce an overhead stream comprising methylbutane, normal pentane and dimethylbutane; a bottoms stream having a boiling point at least greater than normal hexane; and a sidecut stream comprising normal hexane and methylpentane which is withdrawn at a location below the intermediate point. At least a portion of the extract stream and of the sidecut stream are then returned to the isomerization zone as the first and second recycle streams. The overhead stream is passed to a selective adsorption zone that contains at least three adsorbent beds and is contacted with a normal paraffin selective adsorbent at vapor phase conditions and at a first pressure in a first adsorbent bed while cocurrently venting non-adsorbed gas components from and reducing the pressure in a second adsorbent bed that has just undergone adsorption to a second pressure and reducing the pressure in a third adsorbent bed that has just undergone cocurrent venting to a third pressure by countercurrent desorption. An extract stream comprising normal hydrocarbons and a product stream comprising branched hydrocarbons is then withdrawn from the separation zone.

Other aspects of this invention relate to particular process operations and arrangements as described herein. For example, in one aspect, the isomerization zone effluent is passed directly to a stabilizer, $C_4$ and lighter hydrocarbons are removed from the effluent and the remainder of the effluent is passed directly to the selective adsorption zone. In another aspect of this invention, the feedstream contains methylcyclopentane and cyclohexane and the deisohexanizer zone is operated such that the sidecut stream and the bottoms stream contains cyclohexane.

Other embodiments, aspects and details of this invention are further described in the following detailed description of the invention.

DETAILED DESCRIPTION OF THE INVENTION

This invention uses the combination of an isomerization zone and an adsorptive separation section. The invention is not restricted to a particular type of isomerization zone or adsorption section. The isomerization zone can consist of any type of isomerization zone that takes a stream of $C_5$–$C_6$ straight-chain hydrocarbons or a mixture of straight-chain and branched-chain hydrocarbons and converts straight-chain hydrocarbons in the feed mixture to branched-chain hydrocarbons and branched hydrocarbons to more highly branched hydrocarbons thereby producing an effluent having branched-chain and straight-chain hydrocarbons. The adsorption sections is preferably vapor phase and can utilize any type of well known adsorption process such as a swing bed, simulated moving bed, or other schemes for contacting the adsorbent with the feed mixture and desorbing the feed mixture from the adsorbent with the desorbent material. A pressure swing type adsorption system has been found to be most useful for this process, particularly a simplified adsorption process that requires minimal capital investment and provides a relatively low purity normal paraffin product.

Suitable feedstocks for this process will include $C_5$ and $C_6$ hydrocarbons. At minimum, the feed will include normal hexane and normal pentane. The typical feed for this process will be a naphtha feed with an initial boiling point in the range of normal butane. The feedstocks that can be used in this invention include hydrocarbon fractions rich in $C_5$–$C_6$ normal paraffins. The term "rich" is defined as a stream having more than 50% of the mentioned component. Preferred feedstocks are substantially pure normal paraffin streams having from 5 to 6 carbon atoms or a mixture of such substantially pure normal paraffins. It is also preferred that the feed contain at least 10% and preferably at least 20% normal pentanes. Useful feedstocks include light natural gasoline, light straight-run naphtha, gas oil condensates, light reffinates, light reformate, light hydrocarbons, and straight-run distillates having distillation end points of about 77° C. (170° F.) and containing substantial quantities of $C_4$–$C_6$ paraffins. The feed may also contain low concentrations of unsaturated hydrocarbons and hydrocarbons having more than 6 carbon atoms. The concentration of these materials should be limited to 10 wt. % for unsaturated compounds and 20 wt. % for heavier hydrocarbons in order to restrict hydrogen consumption in cracking reactions. The feed and any normal paraffin recycle are combined and typically enter the isomerization zone with a hydrogen recycle stream.

This application is more specifically described with reference to FIG. 1. Reference to the specific flowscheme for this invention shown in FIG. 1 is not meant to limit it to the details disclosed therein.

Figure 1:
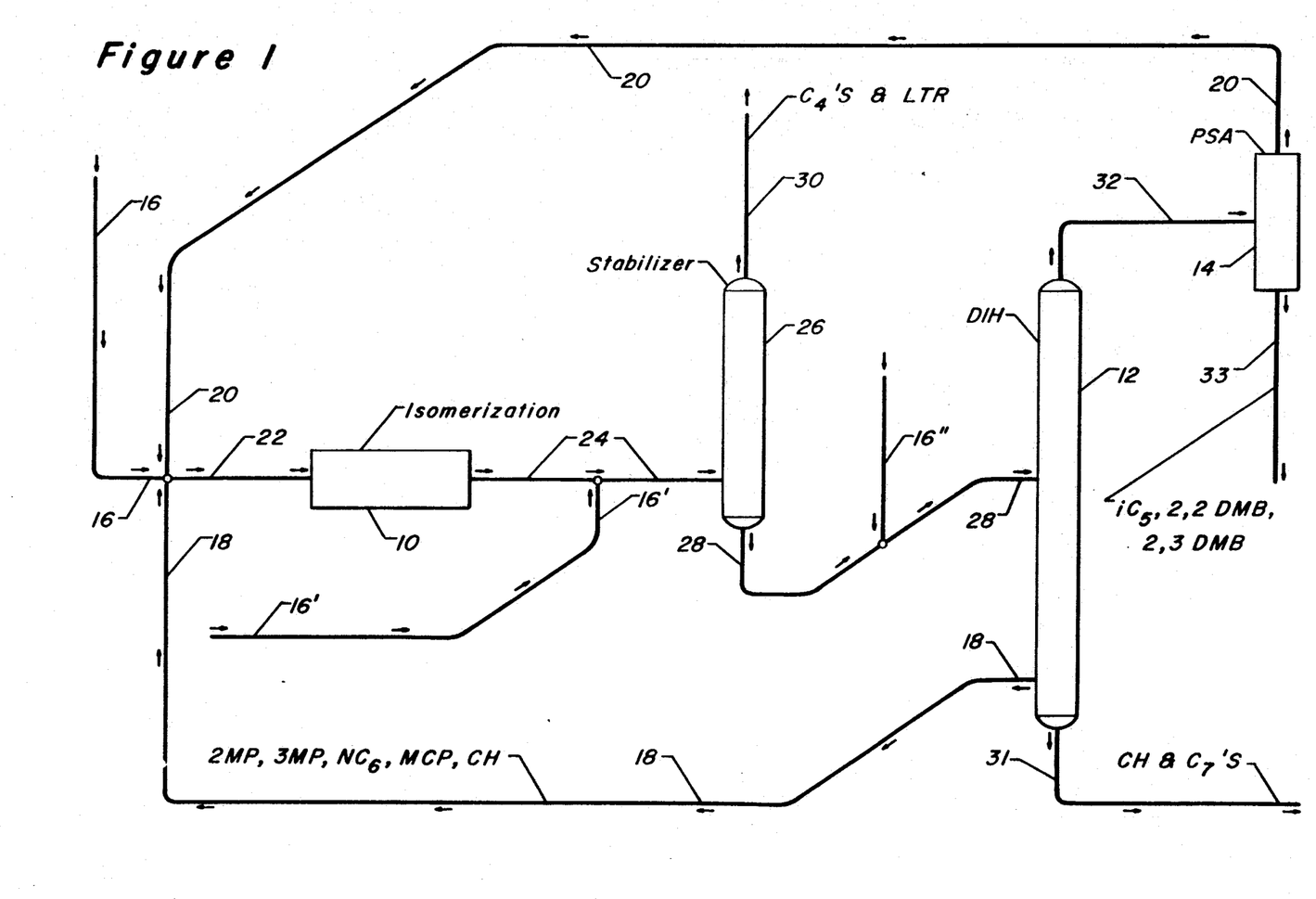
FIG. 1 is a schematic flowscheme of the process of this invention.

As shown in FIG. 1, three essential operating zones make up the basic process. An isomerization zone 10 for isomerizing $C_5$ and $C_6$ hydrocarbons in a combined feedstream comprises one zone. The second zone takes the form of a deisohexanizer fractionation zone 12 for recovering an overhead stream of 2,3-dimethylbutane and lower boiling hydrocarbons, a sidecut stream comprising 2-methylpentane and higher boiling hydrocarbons such an n-$C_6$ and a bottoms stream comprising hydrocarbons boiling at a temperature higher than n-$C_6$ that are not removed with the sidecut stream. A separation zone 14 provides the third zone and separates the overhead stream containing 2,3-dimethylbutane and lower boiling hydrocarbons into an extract stream that comprises normal paraffins and a product stream comprising methylbutane and dimethylbutane.

Fresh feed of the type previously described may enter the process at a number of locations. As shown in FIG. 1, fresh feed from a line 16 is combined with a first recycle stream 20 comprising normal pentane from the separation zone 14 and a second recycle stream 18 from the deisohexanizer zone 12. Alternately, fresh feed may be added to stabilizer zone 26 by a line 16' via line 24, if it contains $C_4$ and lighter hydrocarbons, or directly into the deisohexanizer zone 12, via a line 16" through line 28, to reduce the volume of feed to the isomerization zone 10 by separating out isobutane and dimethylbutanes and heavier hydrocarbons that are withdrawn in the bottoms stream from the deisohexanizer zone. If these alternative addition points are used, at least a portion of the $C_5$ and $C_6$ hydrocarbons of the feedstream are charged to zone 10 along with the recycle streams 18 and 20.

Whether charged directly to the isomerization zone or accompanying the recycle streams 18 and 20, essentially all of the normal paraffins and methylpentanes from the fresh feed are charged to the isomerization zone. The second recycle stream 18, primarily a $C_6$ recycle stream containing any unconverted methylpentanes and normal hexane, insures that all such $C_6$ hydrocarbons are isomerized to higher octane isomers. Likewise, the first recycle stream 20 from separation zone 14, which is essentially a normal pentane recycle stream, recycles substantially all of the normal pentane through the isomerization zone 10 until extinction. A line 22 carries the combined feedstream into isomerization zone 22.

Hydrogen is admixed with the combined feed to the isomerization zone in an amount that will provide a hydrogen to hydrocarbon molar ratio of from 0.01 to 10 in the effluent from the isomerization zone. Preferably, the hydrogen to hydrocarbon ratio is in the range of 0.05 to 5. Although no net hydrogen is consumed in the isomerization reaction, the isomerization zone will have a net consumption of hydrogen often referred to as the stoichiometric hydrogen requirement which is associated with a number of side reactions that occur. These side reactions include saturation of olefins and aromatics, cracking and disproportionation. For feeds having a high level of unsaturates, satisfying the stoichiometric hydrogen will require a higher hydrogen to hydrocarbon ratio for the feed at the inlet of the isomerization zone. Hydrogen in excess of the stoichiometric amounts for the side reactions is often maintained in the reaction zone to provide stability and conversion by compensating for variation in feedstream compositions that alter the stoichiometric hydrogen requirements. Higher hydrogen to hydrocarbon ratios are often used to prolong catalyst life by suppressing side reactions such as cracking and disproportionation. When such side reactions occur, they can reduce conversion and lead to formation of carbonaceous compounds, usually referred to as coke, that foul the catalyst.

It has recently been found that the hydrogen to hydrocarbon ratio in isomerization zones that use a chlorided platinum alumina catalyst can be reduced significantly. In such cases, it is desirable to reduce the amount of hydrocarbon that enters the isomerization zone such that the hydrogen to hydrocarbon ratio of the effluent from the isomerization zone is less than 0.05. Reduced hydrogen to hydrocarbon ratios have been used based on the finding that the amount of hydrogen needed for suppressing coke formation need not exceed dissolved hydrogen levels. The amount of hydrogen in solution at the normal conditions of the isomerization zone effluent are preferably in a ratio of from 0.02 to 0.01. The amount of excess hydrogen over the stoichiometric requirement that is required for good stability and conversion is in a ratio of 0.01 to less than 0.05.

When the hydrogen to hydrocarbon ratio exceeds 0.05, it is not economically desirable to operate the isomerization zone without the recycle of hydrogen to the isomerization zone. Therefore, in such cases, recovery facilities for hydrogen from the effluent will be provided as hereinafter described. Hydrogen may be added to the feed mixture in any manner that provides the necessary control for the addition of the hydrogen.

The hydrogen and hydrocarbon feed mixture is contacted in the reaction zone with an isomerization catalyst. The catalyst composites that can be used in the isomerization zone include traditional isomerization catalysts. Such catalysts include a high chloride catalyst on an alumina base containing platinum, and crystalline aluminosilicates or crystalline zeolites. Suitable catalyst compositions of this type will exhibit selective and substantial isomerization activity under the operating conditions of the process.

The preferred isomerization catalyst for this invention is a chlorided platinum alumina catalyst. The aluminum is preferably an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process. The chloride component termed in the art "a combined chloride" is present in an amount from about 2 to about 10 wt. % based upon the dry support material. The use of chloride in amounts greater than 5 wt. % have been found to be the most beneficial for this process. The inorganic oxide preferably comprises alumina and more preferably gamma-alumina, eta-alumina, and mixtures thereof.

There are a variety of ways for preparing the catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of halogen must be incorporated into the catalyst by the addition or formation of aluminum chloride to or on the platinum-aluminum catalyst base. An alternate method of increasing the halogen concentration in the final catalyst composite is to use an aluminum hydrosol to form the aluminum carrier material such that the carrier material also contains at least a portion of the chloride. Halogen may also be added to the carrier material by contacting the calcined carrier material with an aqueous solution of the halogen acid such as hydrogen chloride.

It is generally known that high chlorided platinum-alumina catalysts of this type are highly sensitive to sulfur and oxygen-containing compounds. Therefore, the use of such catalysts requires that the feedstock be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$-$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feedstream by hydrotreating. A variety of commercial dryers are available to remove water from the feed components. Adsorption processes for the removal of sulfur and water from hydrocarbon streams are also well known to those skilled in the art.

Isomerization zones also commonly employ zeolitic catalysts. As a class, the crystalline aluminosilicate or crystalline zeolite catalysts comprise crystalline zeolitic molecular sieves having an apparent pore diameter large enough to adsorb neopentane. A silica alumina molar ratio $SiO_2:Al_2O_3$ of greater than 3; less than 60 and preferably between 15 and 30 is desirable. In preferred form, the zeolite will contain an equivalent percent alkali metal cations and will have those $AlO_4$-tetrahedra not associated with alkali metal cations; either not associated with any metal cations or associated with divalent or other polyvalent metal cations. Usually the molecular sieve is a mordenite molecular sieve which is essentially in the acid form or is converted to the acid form. Particularly preferred catalysts of this type for isomerization are disclosed in detail in U.S. Pat. Nos. 3,442,794 and 3,836,597.

A preferred composition of zeolitic catalyst for use in the present invention comprises a Group VIII noble metal, a hydrogen form crystalline aluminosilicate, and a refractory inorganic oxide with the catalyst composition having a surface area of at least 580 $m^2/g$. Significant improvements in isomerization performance are realized when the surface area of the catalytic composite is at or above 580 $m^2/g$. A Group VIII metal is incorporated into the catalytic composite to supply a hydrogenation/dehydrogenation function and the preferred Group VIII noble metal is platinum. The Group VIII noble metal is present in an amount from about 0.01 to 5% by weight of the composite and preferably in an amount of at least 0.15% by weight but not over 0.35% by weight. The zeolitic catalytic composite may also contain a catalytically effective amount of a promoter metal such as tin, lead, germanium, cobalt, nickel, iron, tungsten, chromium, molybdenum, bismuth, indium, gallium, cadmium, zinc, uranium, copper, silver, gold, tantalum, or one or more of rare earth metals and mixtures thereof. The hydrogen-formed silica alumina has either a three-dimensional or channel pore structure crystal lattice framework. The three-dimensional aluminosilicates include both synthetic and naturally occurring silica aluminas such as faujasites, which include X-type, Y-type, ultrastable-Y, and the like. L-type, omega-type, and mordenite are examples of the channel pore structure crystalline aluminosilicates. Mordenite, in either naturally occurring or synthetic form are preferred, particularly with a silica to alumina ratio of at least 16:1. The hydrogen form aluminosilicate may be present in an amount within the range of 50 to about 99.5 wt. %, preferably within the range of 75 to about 95 wt. %, and a refractory inorganic oxide may be present in an amount within the range of from 25 to about 50 wt. %.

Operating conditions within the isomerization zone are selected to maximize the production of isoalkane product from the feed components. Temperatures within the reaction zone will usually range from about 40°-320° C. (100°-600° F.). Lower reaction temperatures are generally preferred since they usually favor equilibrium mixtures of isoalkanes versus normal alkanes. Lower temperatures are particularly useful in processing feeds composed of $C_5$ and $C_6$ alkanes where the lower temperatures favor equilibrium mixtures having the highest concentration of the most branched isoalkanes. When the feed mixture is primarily $C_5$ and $C_6$ alkanes temperatures in the range of from 60° to 160° C. are preferred. Higher reaction temperatures increase catalyst activity and promote the isomerization of $C_4$ hydrocarbons. The reaction zone may be maintained over a wide range of pressures. Pressure conditions in the isomerization of $C_4$–$C_6$ paraffins range from 700 to 7000 kPag. Preferred pressures for this process are in the range of from 2000 to 3000 kPag. The feed rate to the reaction zone can also vary over a wide range. These conditions include liquid hourly space velocities ranging from 0.5 to 12 hr.$^{-1}$, however, space velocities between 1 and 6 hr.$^{-1}$ are preferred. The isomerization zone will usually operate at a LHSV of about 1.5.

Operation of the reaction zone with the preferred chlorided platinum-alumina catalyst also requires the presence of a small amount of an organic chloride promoter. The organic chloride promoter serves to maintain a high level of active chloride on the catalyst as low levels are continuously stripped off the catalyst by the hydrocarbon feed. The concentration of promoter in the reaction zone is maintained at from 30 to 300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which converts to hydrogen chloride. As long as the process streams are kept dry, there will be no adverse effect from the presence of hydrogen chloride.

The isomerization zone usually includes a two-reactor system with a first stage reactor and a second stage reactor in the reaction zone. The catalyst used in the process is distributed equally between the two reactors. It is not necessary that the reaction be carried out in two reactors but the use of two reactors confer several benefits on the process. The use of two reactors and specialized valving allows partial replacement of the catalyst system without taking the isomerization unit off stream. For the short periods of time during which replacement of catalyst may be necessary, the entire flow of reactants may be processed through only one reaction vessel while catalyst is replaced in the other. The use of two reaction zones also aids in maintaining lower catalyst temperatures. This is accomplished by having any exothermic reaction such as hydrogenation of unsaturates performed in a first reaction vessel with the rest of the reaction carried out in a final reaction vessel at more favorable temperature conditions.

The effluent from the isomerization reaction zone usually enters a stabilizer that removes light gases and butane from the effluent. FIG. 1 shows a line 24 transferring the isomerization zone effluent to a stabilizer 26. The need for a stabilizer and the amount of butane taken off from the stabilizer will vary depending upon the amount of butane entering the process. The stabilizer normally runs at a pressure of from 800 to 1700 kPaa.

When the isomerization zone is operated with a high hydrogen to hydrocarbon ratio, a separator (not shown) is usually placed ahead of the stabilizer. A hydrogen-rich recycle gas stream is recovered from the separator and recycled for combination with the feed entering the isomerization zone. When the isomerization zone operates with very low hydrogen to hydrocarbon ratios the separator is not needed and the effluent from the isomerization zone may enter the stabilizer directly.

The bottoms stream from stabilizer 26 provides at least a portion of the isomerization zone effluent stream and is taken by line 28. It comprises $C_5$ and higher boiling hydrocarbons that include normal paraffins for recycle and isoparaffin products. $C_4$ and lighter hydrocarbons are taken overhead by line 30 and recovered for further processing or fuel gas use. The chlorides which may be present in the reaction zone will usually pose no problem for downstream processing. In normal operation, any chlorides that are present in the effluent from the isomerization zone will be removed in the overhead from the stabilizer. However, where the isomerization zone or separators downstream from the isomerization are subject to upsets, it may be desirable to provide a guard bed of some type to treat the stabilizer bottoms and prevent any carryover of chloride compounds into the adsorption section.

In the operation of this process, at least a portion of the isomerization effluent will be passed to distillation zone 12 either directly or via stabilizer 26 and line 28. The distillation zone will typically be in the form of a single fractionation column operated as a deisohexanizer as shown in FIG. 1. The general design and operation of such fractionation zones is well known to the separation art.

The distillation zone serves a variety of purposes. It provides an overhead stream that contains a high concentration of normal pentane, methylbutane and dimethylbutanes. The distillation zone also provides the previously referred to $C_6$ recycle stream that comprises normal hexane and monomethylpentanes. These relatively lower octane hydrocarbons can be recovered from the distillation zone in any manner. Preferably the $C_6$ recycle stream exits as a sidecut from the single deisohexanizer column. In FIG. 1, line 18 represents the sidecut stream withdrawn from the deisohexanizer column 12. As represented in FIG. 1, a tray location below the input point of the stabilized effluent stream supplies sidecut stream 18. In the operation of a fractionation zone having the arrangement of deisohexanizer 12, the cut point for the sidecut stream is below the boiling point of 2,3-dimethylbutane and above the boiling point of 2-methylpentane. 2,3-dimethylbutane has the higher octane of the dimethylbutane isomers and 2-methylpentane has a relatively low octane number, lower than 3-methylpentane. As a result, a good split between the sidecut and the overhead is desired to maximize octane. Since only a narrow boiling point difference separates 2,3-dimethylbutane and 2-methylpentane, the deisohexanizer is designed to maximize this separation.

The lower cut point for the deisohexanizer zone is particularly important to the operation of this process. It should be set low enough to recycle essentially all of the methylpentane and normal hexane to the isomerization zone. Preferably, the deisohexanizer column will operate with a lower cut point set at about the boiling point of cyclohexane. With a cyclohexane cut point a substantial portion of cyclohexane and all methylcyclopentane will be recycled to the isomerization zone.

Heavier hydrocarbons are withdrawn from the distillation zone as a heavy hydrocarbon stream. For the single column deisohexanizer, this heavy hydrocarbon stream is withdrawn by a line 31. Where a full boiling range naphtha is used as the feed to the process, the heavy hydrocarbon feed will comprise a $C_7$+naphtha. This bottoms stream will ordinarily be used as the feed in a reforming zone. A cyclohexane cut point between the sidecut and heavy hydrocarbon stream introduce substantial portions of any cyclohexane into the heavy hydrocarbon stream. Such an operation will maximize the production of aromatics from a downstream reforming zone.

The remainder of the isomerization zone effluent comprising 2,3-dimethylbutane and lower boiling hydrocarbons is taken from the deisohexanizer column and transferred to the separation section. For this purpose, FIG. 1 illustrates removal of the lower boiling isomerization zone fraction from the deisohexanizer column 12 by an overhead line 32 that carries the fraction to separation section 14. The adsorption section of this invention is operated to primarily remove the normal pentane fraction from the effluent of the isomerization zone which is returned to the isomerization zone by line 20. The isomerization zone products are recovered by a line 33.

A number of different adsorption processes will separate normal pentane from other $C_5$ and $C_6$ isoparaffins. For use in this process, the adsorption system should operate to efficiently recover the normal pentane at relatively low cost. A low cost system is possible since the normal pentane recycle stream does not require a high purity. Apart from the additional throughput, the recycle of additional dimethylbutanes has no adverse impact on the process.

This process is especially suited for a pressure swing adsorption (PSA) systems that uses multiple beds for the steps of adsorption under pressure, and depressurization desorption. Relatively simple PSA systems can be used in this invention since there is no need to maintain a high purity for the $C_5$ recycle stream.

A number of specially defined terms are used in describing the simulated adsorption processes. The term "feedstream" indicates a stream in the process through which feed material passes to the molecular sieve for adsorption. A feed material comprises one or more extract components and one or more raffinate components. An "extract component" is a compound or type of compound that is more selectively retained by the molecular sieve while a "raffinate component" is a compound or type of compound that is less selectively retained. The term "raffinate output stream" means a stream through which most of the raffinate components are removed from the molecular sieve. The term "selective pore volume" of the molecular sieve is defined as the volume of the molecular sieve which selectively retains extract components from the feedstock. The term "non-selective void volume" of the molecular sieve is the volume of the molecular sieve which does not selectively retain extract components from the feedstock. This non-selective void volume includes the cavities of the molecular sieve which are not capable of retaining extract components and the interstitial void spaces between molecular sieve particles. The selective pore volume and the non-selective void volume are generally expressed in volumetric quantities and are of importance in determining the proper flow rates of fluid required to be passed into an operational zone for efficient operations to take place for a given quantity of molecular sieve.

The present invention can be carried out using virtually any adsorbent material in the adsorption section that has capacity for the selective adsorption of either isoparaffin or the normal paraffin components. Suitable adsorbents known in the art and commercially available include crystalline molecular sieves, activated carbons, activated clays, silica gels, activated aluminas and the like. The molecular sieves include, for example, the various forms of silicoaluminophosphates and aluminophosphates disclosed in U.S. Pat. Nos. 4,440,871; 4,310,440 and 4,567,027, hereby incorporated by reference, as well as zeolitic molecular sieves.

Zeolitic molecular sieves in the calcined form may be represented by the general formula:

$$\mathrm{Me}_{\frac{2}{n}}\mathrm{O}:\mathrm{Al}_2\mathrm{O}_3:x\mathrm{SiO}:y\mathrm{H}_2\mathrm{O}$$

where Me is a cation, x has a value from about 2 to infinity, n is the cation valence and y has a value of from about 2 to 10.

Typical well-known zeolites which may be used include, chabazite, also referred to as Zeolite D, clinoptilolite, erionite, faujasite, also referred to as Zeolite X and Zeolite Y, ferrierite, mordenite, Zeolite A, and Zeolite P. Other zeolites suitable for use according to the present invention are those having a high silica content, i.e., those having silica to alumina ratios greater than 10 and typically greater than 100. One such high silica zeolite is silicalite, as the term used herein includes both the silicapolymorph disclosed in U.S. Pat. No. 4,061,724 and also the F-silicate disclosed in U.S. Pat. No. 4,073,865, hereby incorporated by reference. Detailed descriptions of some of the above-identified zeolites may be found in D. W. Breck, *Zeolite Molecular Sieves*, John Wiley and Sons, New York, 1974, hereby incorporated by reference. Preferred adsorbents for the PSA type adsorption section include a type 5 A molecular sieve in the form of ⅛ pellets. The selection of other adsorbents for normal hydrocarbon separation can be made by one skilled in the art with routine experimentation. This invention is further described in the context of an adsorbent that preferably absorbs normal paraffins and rejects isoparaffins such as a type 5 A molecular sieve.

It is often desirable when using crystalline molecular sieves that the molecular sieve be agglomerated with a binder in order to ensure that the adsorbent will have suitable physical properties. Although there are a variety of synthetic and naturally occurring binder materials available such as metal oxides, clays, silicas, aluminas, silica-aluminas, silica-zirconias, silica thorias, silica-berylias, silica-titanias, silica-aluminas-thorias, silica-alumina-zirconias, mixtures of these and the like, clay-type binders are preferred. Examples of clays which may be employed to agglomerate the molecular sieve without substantially altering the adsorptive properties of the zeolite are attapulgite, kaolin, volclay, sepiolite, polygorskite, kaolinite, bentonite, montmorillonite, illite and chlorite. The choice of a suitable binder and methods employed to agglomerate the molecular sieves are generally known to those skilled in the art.

The PSA cycle of the present invention can include the well-known cycle steps of adsorption, one or more optional equalization steps, countercurrent desorption, an optional purge step and repressurization. The cycle steps are typically described with reference to their direction relative to the adsorption step. Thus, cycle steps wherein the gas flow is in a concurrent direction to the adsorption step are known as "cocurrent" steps. Similarly, cycle steps wherein the gas flow is countercurrent to the adsorption step are known as "countercurrent" steps. During the adsorption step, the feedstream is passed to the adsorber bed at an elevated adsorption pressure in order to cause the adsorption of the adsorbate and provide a product stream enriched in hydrogen relative to feedstream. During the equalization steps the pressure in the depressurizing bed is released preferably cocurrently and the effluent obtained therefrom, which is preferably rich in the adsorbed component, is passed in a countercurrent direction to another adsorber undergoing repressurization. Typically, at the conclusion of the equalization steps, a provide purge step is initiated wherein the adsorber bed is further cocurrently depressurized to provide a purge gas that is relatively impure with respect to and thus is suitable for use as a purge gas. Optionally, instead of the provide purge step a portion of the product gas or gas obtained from one of the equalization steps can be used to supply a purge gas. Upon completion of the provide purge step, if employed, the adsorber bed is countercurrently depressurized to a desorption pressure in order to desorb the adsorbate. Upon completion of the desorption step, the adsorber bed may be purged countercurrently with purge gas obtained from another adsorber bed. Finally, the adsorber bed is repressurized, first, with equalization gas from other adsorber beds, if an equalization step is employed, and then with feed or product gas to adsorption pressure. Other additional steps known to those skilled in the art, such as for example, a copurge step wherein the adsorber bed is cocurrently purged at an elevated pressure such as the adsorption pressure with a purge stream comprising the adsorbate, can be employed.

The temperatures used in the adsorption process of the present invention are not critical, although in general the process is substantially isothermal. Typical temperatures range between about 50°–600° F., and preferably within the range of about 200°–500° F., and even more preferably from about 400°–500° F. It is preferred, in accordance with the present invention, that the process steps described above be performed at substantially the same temperature as the rest of the cycle. It is to be understood, however, that even though the process is generally isothermal, there is to be expected a certain degree of temperature increase and decrease associated with the thermal effects of the heats of adsorption and desorption.

Similarly, the absolute pressure levels employed during the PSA process are not critical provided that the pressure differential between the adsorption and desorption steps is sufficient to cause a change in the adsorbate fraction loading on the adsorbent thereby providing a delta loading effective for separating the feedstream. Typical pressure levels range from about 50 to 2000 psia, more preferably from about 80 to 500 psia, and even more preferably from about 80 to about 120 psia, during the adsorption step; and from about 0.5 to 200 psia, more preferably from about 0.5 to 50 psia and even more preferably from about 0.5 to about 10 psia, at the end of the final desorption step. The pressures during any equalization or blowdown steps, provide purge step, first countercurrent desorption step and countercurrent purge step are intermediate between the adsorption and the final desorption steps. Preferably cocurrent venting will reduce the adsorbent bed pressure to within a range of 30 to 15 psia.

In general the total cycle time, that is, the time required to perform all the individual steps in the PSA cycle ranges from about 3 to 30 minutes, and more preferably within the range of about 4 to 20 minutes. At least two adsorber beds are required in order to perform each equalization step and typically at least three adsorber beds and one additional vessel are required in order to provide a constant source of product gas.

Figure 2:
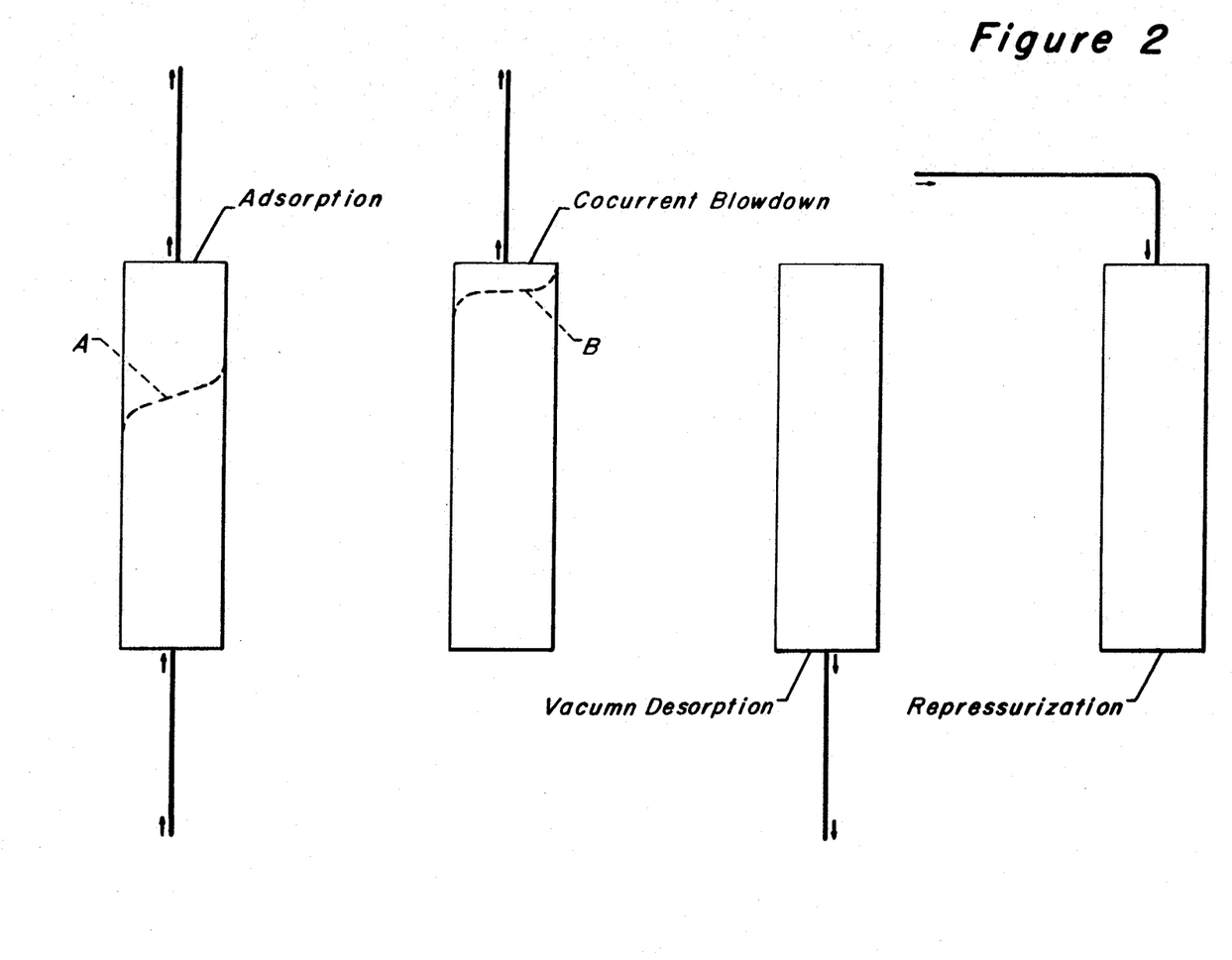
FIG. 2 is a schematic representation of the adsorption zone of this invention.

It has been found that a relatively simple PSA system will provide the most benefit for this invention. FIG. 2 shows the most basic series of steps that are performed on each bed in the adsorption zone. This type of system uses four operational steps that are shown schematically in FIG. 2. The first step is adsorption in which the PSA feedstream passes isothermally and isobarically through an adsorption stage as the adsorption feed passes through the adsorbent bed. In a typical process, the adsorption zone is operated at a temperature of 500°, a pressure of 100 psia and feed is passed through the zone for approximately four minutes. A mass transfer point is formed having a stoichiometric point indicated by line A. The stoichiometric point for the mass transfer zone, also referred to as an impurity adsorption front, is allowed to pass only partially up the bed. In usual practice this front will only pass between 55 to 75% of the length of the bed as measured at the mid point of the front. Vapor in the adsorption stream that is upstream of the stoichiometric point has the composition of the separation zone feed. The selective pore volume of the adsorbent upstream of the stoichiometric point contains normal hydrocarbons that have been adsorbed from the feedstream. Downstream of the stoichiometric point, the void space of the adsorption zone contains relatively pure isoparaffin feedstream components.

After adsorption and well before the stoichiometric point of the mass transfer zone has reached the end of the adsorption zone, feedstream flow to the adsorption zone has stopped and the cocurrent blowdown step begins. In this step pressure is released from the outlet end of the adsorbent bed. As pressure is released, the stoichiometric point of the mass transfer zone advances towards the end of the bed. During the cocurrent blowdown step, pressure is reduced from the 100 to about 20 psia over a 2 to 3-minute period. As the pressure is reduced, normal hydrocarbons from the selective void volume of the adsorbent are desorbed and re-adsorbed along with additional normal hydrocarbons from the feed as both the feed and hydrocarbons advance beyond stoichiometric point A to the re-established stoichiometric point B. A relatively pure raffinate stream of isoparaffins is again recovered from the outlet of the bed during the cocurrent blowdown step. This raffinate from the cocurrent blowdown step can be recovered as additional isoparaffin product or transferred to another adsorbent bed to provide repressurization in a manner hereinafter described. After stoichiometric point B has advanced up the bed for a predetermined distance, usually about 55 to 100% of the bed length, the outlet of the adsorbent bed is closed.

The next step is vacuum desorption for the removal of the adsorbed normal hydrocarbons. A vacuum pressure created on the inlet line to the adsorption bed evacuates the void space fluid and releases adsorbed normal hydrocarbons from the selective void volume of the adsorbent. Since the fluid in the void volume has the feed mixture composition, the extract effluent from the vacuum desorption step has a relatively low purity as a result of contamination from isoparaffin components in the feed mixture. Withdrawal of extract stream continues until the vacuum desorption zone pressure is reduced to about 1 psia over a time period of about four minutes. Extract from the vacuum desorption zone provides the second recycle stream that contains normal pentanes and any other normal hydrocarbons that enter the separation zone.

Repressurization prepares the adsorbent bed for the next adsorption step by increasing the pressure in the adsorbent bed from approximately 1 to 100 psia. Repressurization takes approximately 1 to 2-minute and typically uses the raffinate stream from a simultaneous adsorption step to effect the repressurization. It is also possible to use the raffinate vented from the blowdown step during the initial stages of repressurization. Passing the raffinate stream into the outlet end of the adsorbent bed during the repressurization step clears normal paraffins from the outlet of the bed so that the raffinate is not contaminated during the adsorption step.

A number of methods are known for operating the adsorption zone that will minimize the required amount of adsorbent and increase the purity or recovery from the adsorption section. A more complete description of a suitable PSA system is shown in U.S. Pat. No. 3,176,444, the contents of which are hereby incorporated by reference.

Figure 3:
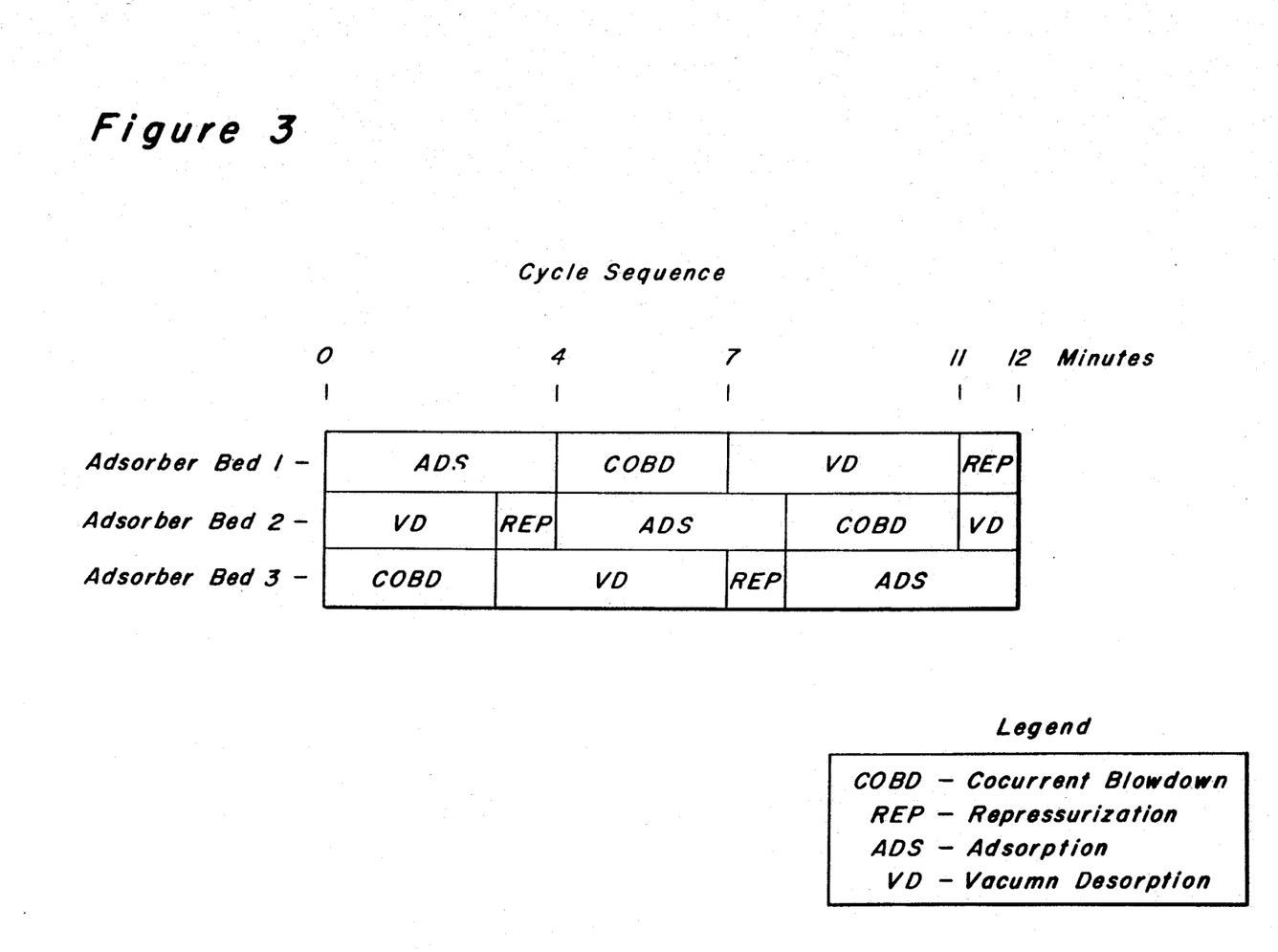
FIG. 3 is a block diagram of the cycle sequence for the adsorption section of this invention.

A schematic representation of the cycle sequence described for the adsorption steps in FIG. 2 is shown in FIG. 3. The cycle sequence is for a three-adsorber bed system and shows the operation of each bed during a complete adsorption cycle. At time zero, the cycle begins with bed 1 undergoing adsorption, bed 2 undergoing vacuum desorption and bed 3 undergoing cocurrent blowdown. The time for adsorption and vacuum desorption in the cycle sequence are the same. Cocurrent blowdown and repressurization occur over a shorter period that in total is equal to the time period of adsorption or vacuum desorption. The cycle sequence shows that cocurrent blowdown and repressurization occur over different time periods for each of the beds. As a result, in a three-bed system, raffinate from the cocurrent blowdown step is not simultaneously available for a bed undergoing repressurization. In addition, there is a substantial overlap between the time over which one bed is undergoing cocurrent blowdown and another bed is undergoing adsorption. This results in an unsteady flow of raffinate from the adsorption section in which a high flowrate of raffinate occurs during the simultaneous cocurrent blowdown and adsorption phase and a very low flow of raffinate when it is needed for the repressurization of another bed. Therefore, this three-bed arrangement is provided with a surge drum for receiving the raffinate stream and providing a steady flow of raffinate from the adsorption section while also making an increased flow of raffinate available during the repressurization step. Additional flowschemes are known that use four or more beds to eliminate or reduce the surge of raffinate. These schemes are shown in U.S. Pat. No. 3,176,444.

EXAMPLE

Figure 4:
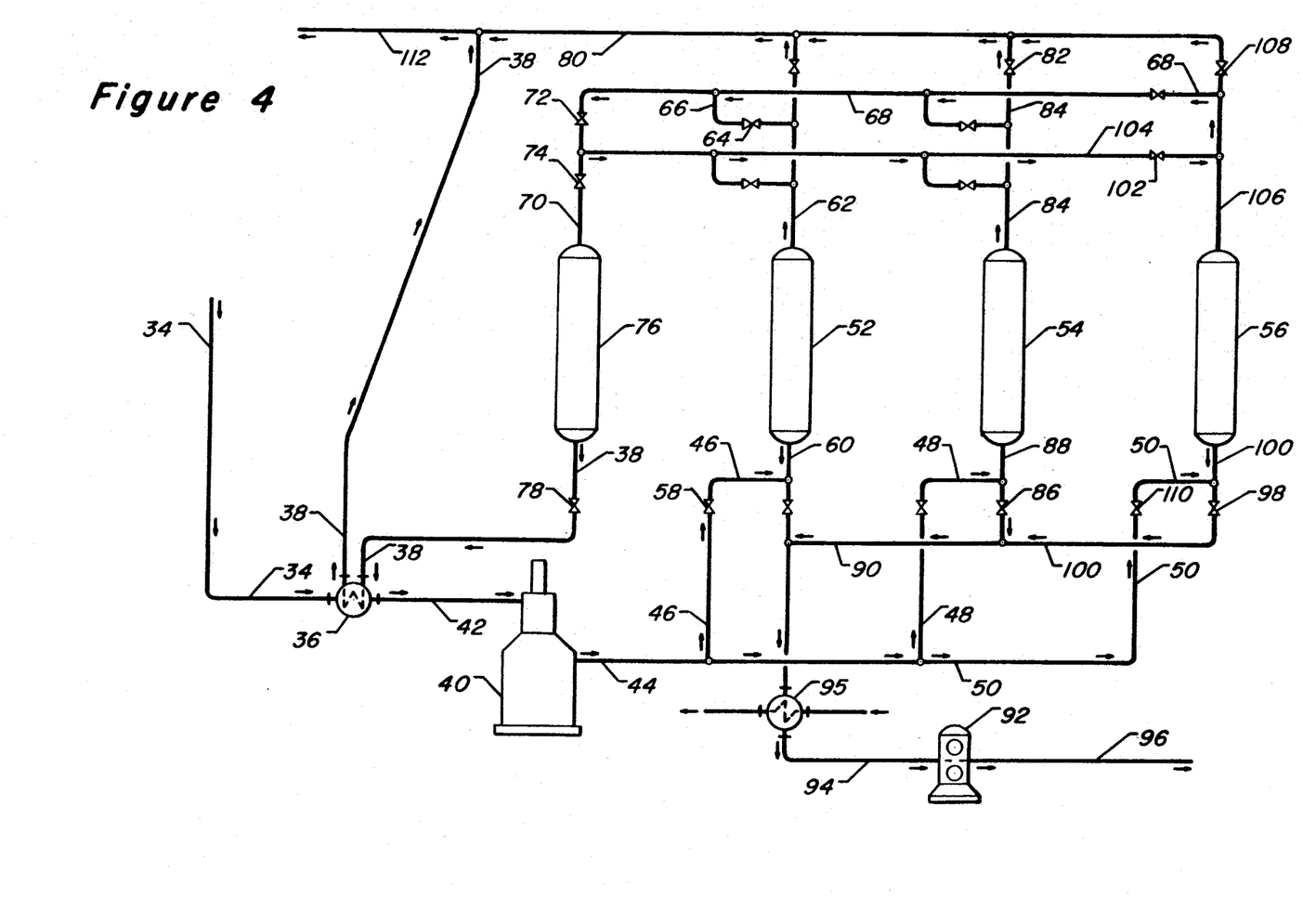
FIG. 4 is a schematic diagram of an adsorption section used in the process of this invention.

A detailed operation of the three-adsorbent bed and surge drum arrangement for the separation zone of this invention is shown in FIG. 4. A limited example of this invention is shown in conjunction with FIG. 4 and FIG. 1. The Example is provided for illustrative purposes and is not intended to limit the scope of the claims. The three-adsorber bed PSA process with an adsorption blowdown and desorption steps were simulated using a computer simulation model that is commonly used for designing PSA processes. The composition of the various process streams is given in the accompanying table. The overall arrangement of the process is the same is that shown in FIG. 1. A feedstream having a composition given in the Table for line 16 is combined at a rate of 69,293 lbs/hr with first and second recycle streams having the compositions given under lines 18 and 20 in the attached Table and at rates of 43,164 and 8,459 lbs/hr, respectively. The combined feedstream is contacted with a chlorided platinum aluminum catalyst in a two-bed isomerization system at pressures ranging from 450 to 550 psia and temperatures of from 250° to 350° F. After stabilization and recovery of hydrogen, the effluent from the isomerization zone has the composition given in the Table for line 28 and is transferred to the deisohexanizer column at a rate of 117,131 lbs/hr.

Deisohexanizer column 12 is arranged with 80 trays and operates with a molar reflux to net deisohexanizer overhead ratio of 4.5. The isomerization effluent stream enters the deisohexanizer at tray level 25 and a rate of 117,131 lbs/hr. The first recycle stream having the previously described composition is withdrawn from the deisohexanizer as a sidecut at tray level 69 and a rate of 43,164 lbs/hr. A bottoms stream comprising 83% cyclohexane and higher boiling hydrocarbons is withdrawn from the bottom of the deisohexanizer column by line 31 at a rate of 6,271 lbs/hr. The overhead from the deisohexanizer has the composition given in the Table under line 32 and is transferred to the PSA separation zone shown in FIG. 4. All valves shown in FIG. 4 are in a closed position unless otherwise indicated.

TABLE 1

| | LV % | | | | | | |
|---|---|---|---|---|---|---|---|
| | 16 | 18 | 20 | 28 | 32 | 96 | 112 |
| Isobutane | 0.2 | — | — | — | — | — | — |
| Normal Butane | 2.0 | — | — | — | — | — | — |
| Isopentane | 12.0 | — | 3.9 | 21.5 | 35.9 | 3.9 | 40.6 |
| Normal Pentane | 22.6 | — | 87.4 | 6.6 | 11.1 | 87.4 | 0 |
| Cyclopentane | 2.6 | TR | 0.2 | 1.1 | 1.8 | 0.2 | 2.1 |
| 2,2-Dimethylbutane | 0.2 | 1.0 | 3.3 | 17.8 | 29.1 | 3.3 | 32.9 |
| 2,3-Dimethylbutane | 1.3 | 5.4 | 0.7 | 5.5 | 6.0 | 0.7 | 6.8 |
| 2-Methylpentane | 10.7 | 25.7 | 1.4 | 16.7 | 12.6 | 1.4 | 14.2 |
| 3-Methylpentane | 6.0 | 21.4 | 0.3 | 9.4 | 3.0 | 0.3 | 3.3 |
| Normal Hexane | 19.5 | 16.8 | 2.8 | 6.5 | .4 | 2.8 | 0 |
| Methylcyclopentane | 9.5 | 15.9 | — | 6.1 | .1 | — | 0.1 |
| Cyclohexane | 8.0 | 13.2 | — | 7.2 | TR | — | — |
| Benzene | 2.4 | 0 | — | 0 | — | — | — |
| C7+ | 3.0 | 0.6 | — | 1.6 | — | — | — |

The overhead has a flowrate of 67,695 lbs/hr and enters the process at a pressure of 140 psig and a temperature of 100° F. through a line 34. An exchanger 36 transfers heat from a raffinate effluent stream carried by a line 38 to the incoming feed which flows to a heater 40 by line 42. Heater 40 raises the temperature of the overhead feed from 268° to 500° F. Line 44 transfers the heated overhead feed to a manifold arrangement comprising lines 46, 48 and 50 which during the adsorber sequence supply heated overhead feed to adsorbent beds 52, 54 and 56, respectively. The stage of operation depicted by FIG. 4 shows an open valve 58 that communicates the heated overhead feedstream to the adsorbent bed 52 at a pressure of 100 psia via a line 60. Adsorbent bed 52 is in the adsorption mode and a raffinate stream leaves the bed through an upper line 62. An open valve 64 across a line 66 directs feed into a header 68. A line 70 carries raffinate across open valves 72 and 74 and into surge drum 76. A valve 78 located across line 38 regulates the discharge of raffinate from the surge drum. Raffinate is carried by line 38 through the overhead feed exchanger and into admixture with the hereinafter described raffinate stream from a manifold line 80. During the first 3 minutes of adsorption in bed 52, bed 54 is in the blowdown mode. Valve 82 across line 84 is open to depressurize and regulate the flow of raffinate out of bed 54 and into header 80. Blowdown is continued until pressure in adsorbent bed 54 is reduced to approximately 20 psia. Following three minutes of blowdown, valve 82 is closed and valve 86 across a line 88 is open to begin a vacuum desorption of bed 54 by the withdrawal of extract from line 88 through a header 90. A vacuum pump 92 draws a vacuum on line 94 to evacuate the extract from bed 54 via lines 88 and 90 and provide the second recycle stream. Extract withdrawn during the desorption step passes through a cooler 95 that reduces the extract temperature from 500° to 100°. At the end of the vacuum desorption step the pressure in desorbent bed 56 falls to approximately 1 psia. The recycle stream is taken from suction pump 92 by a line 96 at a rate of 8,459 lbs/hr and has the composition given in Table 1. When bed 52 begins the adsorption step, bed 56 has gone through one minute of a vacuum desorption step. Vacuum desorption for bed 56 is carried out in a manner similar to that described for bed 54 wherein a valve 98 is in an open position to communicate the inlet of the bed with suction header 90 through a line 100. Vacuum desorption of bed 56 continues for another three minutes while bed 52 continues to undergo adsorption and bed 54 undergoes cocurrent blowdown. As adsorption continues in bed 52, and bed 54 is changed from the cocurrent blowdown step to the vacuum desorption step, valve 98 in line 100 closes and bed 56 begins repressurization. During repressurization a valve 102 across a pressurization header 104 opens and raffinate from line 70 flows into the outlet of bed 56. Valve 74 and 72 are throttled to limit flow to surge drum 76 and provide the necessary flow of raffinate to adsorbent bed 56. After approximately one minute of repressurization, valve 102 closes and a valve 108 across line 106 opens and a valve 110 across line 50 opens to put adsorbent bed 56 in the adsorption mode.

The process then continues with bed 52 beginning the cocurrent blowdown step, bed 54 continuing in the vacuum desorption mode and bed 56 beginning the adsorption mode. While one of the beds is in the repressurization mode, only one bed is in the adsorption mode, one is in vacuum desorption mode, and none of the beds are in the cocurrent blowdown mode. As a result, there is minimal raffinate flow available for recovery of the product stream. During this mode, valve 78 on line 38 opens further as the surge drum pressure drops to about 50 psia to supply a continued flow of raffinate across heat exchanger 36 and to line 112 that withdraws the isomerate product stream from the process. The composition of the product withdrawn from line 112 is shown in Table 2 and is recovered at a rate of 59,237 lbs/hr.

The primary function of the surge drum as previously mentioned is to provide a constant flow of raffinate across overhead feed heater 36. During the cocurrent blowdown step, an additional mass of raffinate accumulates in surge drum 76 which restores the pressure to about 100 psia. At the end of the repressurization step, pressure in surge drum 76 drops to about 50 psia. As an alternative to using the surge drum, it is also possible to supply a constant source of heat for raising the temperature of the feedstream by heat exchanging the feedstream against the extract that is withdrawn during the desorption mode. Accordingly, the function of cooler 95 can be replaced, at least in part, by heat exchange with the incoming feed. Heat exchanging the overhead feed against the extract and raffinate stream can have heat conservation advantages.

The product stream has the properties given in table 2.

TABLE 2

| RONC | 91.3 |
|------|------|
| MONC | 89.9 |
| RVP  | 13.7 |
| S.G. | 0.6459 |

This example shows that the isomerate product has a high octane number, 3 to 4 octane numbers higher than that usually achievable with conventional recycle isomerization schemes. Therefore, the flow arrangement of this invention will improve the operation of an isomerization zone and adsorption section combination by increasing the octane of the isomerate obtained therefrom and simplifying the overall operation of the combination process.

What is claimed is:

1. A process for the isomerization of a feedstream comprising $C_5$ and $C_6$ hydrocarbons said process comprising:
   (a) charging a first recycle stream and a second recycle stream into an isomerization zone, passing at least a portion of the $C_5$ and $C_6$ hydrocarbons of the feedstream into the isomerization zone directly or as a portion of at least one of said recycle streams, and contacting said recycle streams and said feedstream hydrocarbons with an isomerization catalyst at isomerization conditions effective to increase the branching of the hydrocarbons charged thereto and to produce an isomerization effluent stream comprising normal pentane, normal hexane, methylbutane, dimethylbutane, and methylpentane;
   (b) passing at least a portion of said isomerization effluent stream to a deisohexanizer zone to distill said effluent stream and to produce an overhead stream comprising methylbutane, normal pentane, and dimethylbutane; a bottoms stream having a boiling point at least greater than normal hexane; and a sidecut stream comprising normal hexane and methylpentane;
   (c) passing said overhead stream to a selective adsorption zone and therein contacting said overhead stream with an adsorbent at conditions effective to separate said overhead stream into an extract stream comprising normal hydrocarbons and a product stream comprising branched hydrocarbons;
   (d) passing at least a portion of said extract stream and of said sidecut stream to step (a) as said first and second recycle streams; and,
   (e) recovering said product stream.

2. The process of claim 1 wherein said adsorption zone is operated under vapor phase conditions.

3. The process of claim 1 wherein said isomerization effluent is passed directly to a stabilizer operated at conditions selected to remove $C_4$ and lighter hydrocarbons from said effluent and the remainder of the effluent is passed directly to said deisohexanizer zone.

4. The process of claim 1 wherein the adsorbent in said adsorption zone comprises a 5A molecular sieve.

5. The process of claim 1 wherein said isomerization catalyst comprises from 0.01 to 0.25 wt. % platinum and from 2 to 10 wt. % of a chloride component and alumina.

6. The process of claim 1 wherein said adsorption zone comprises at least three operationally distinct beds of adsorbent and said beds are operated in, an adsorption mode wherein normal hydrocarbons are adsorbed from said overhead stream at a first pressure, a blowdown mode that cocurrently vents non-adsorbed gas components from and reduces the pressure in a bed that has just undergone adsorption to a second pressure, and a desorption mode that reduces the pressure in a bed that has just undergone blowdown mode to a third pressure while countercurrently recovering normal hydrocarbons.

7. The process of claim 1 wherein the entire feedstream is charged to step (a).

8. The process of claim 1 wherein at least a portion of the feedstream is charged to the deisohexanizer zone.

9. The process of claim 3 wherein at least a portion of the feedstream is charged to the stabilizer.

10. The process of claim 3 wherein the feedstream is charged to one of said stabilizer or said deisohexanizer zone, or directly to said isomerization zone.

* * * * *